US006635043B2

(12) United States Patent
Daubert et al.

(10) Patent No.: US 6,635,043 B2
(45) Date of Patent: Oct. 21, 2003

(54) CONTAINER CAP ASSEMBLY HAVING AN ENCLOSED PENETRATOR

(75) Inventors: Richard F. Daubert, Arlington Heights, IL (US); Steven P. Hellstrom, Schaumburg, IL (US); Peter J. Karas, Libertyville, IL (US); John K. Moore, Evanston, IL (US); John S. Norman, Gurnee, IL (US); John C. Tanner, II, Lake Bluff, IL (US); Donald Verlee, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 149 days.

(21) Appl. No.: 09/754,432

(22) Filed: Jan. 4, 2001

(65) Prior Publication Data

US 2001/0001116 A1 May 10, 2001

Related U.S. Application Data

(62) Division of application No. 09/282,959, filed on Apr. 1, 1999, which is a division of application No. 08/808,330, filed on Feb. 28, 1997, now Pat. No. 5,891,129.

(51) Int. Cl.[7] ........................ A61B 19/00; B65D 47/00; B65D 41/00; B65D 41/32

(52) U.S. Cl. ....................... 604/411; 604/415; 604/905; 215/247; 215/316; 220/266

(58) Field of Search ............................. 604/82, 87, 88, 604/90, 91, 93.01, 403, 411–12, 414–416, 425, 905; 206/219, 220, 222; 215/247, 249, 250, 294, 316, 317, 324–329, 341, 355, 353–54, 320; 220/253, 260, 265–67, 277, 694; 141/329–30

(56) References Cited

U.S. PATENT DOCUMENTS

| | | | | |
|---|---|---|---|---|
| 2,334,905 | A | | 11/1943 | Cherkin |
| 2,342,215 | A | | 2/1944 | Perelson |
| 2,388,634 | A | | 11/1945 | De Woody |
| 2,524,365 | A | | 10/1950 | Smith |
| 2,608,972 | A | | 9/1952 | Chrigstrom |
| 2,653,609 | A | | 9/1953 | Smith |
| 2,659,370 | A | | 11/1953 | Smith |
| 2,667,986 | A | | 2/1954 | Perelson |
| 3,343,699 | A | | 9/1967 | Nicko |
| 3,610,297 | A | | 10/1971 | Raaf |
| 3,662,752 | A | * | 5/1972 | Yokoyama .................. 604/405 |
| 3,729,031 | A | | 4/1973 | Baldwin |
| 3,810,469 | A | | 5/1974 | Hurschman |

(List continued on next page.)

FOREIGN PATENT DOCUMENTS

| | | |
|---|---|---|
| DE | 14 77 025 | 8/1970 |
| DE | 3152033 A1 | 7/1983 |
| DE | 85 32 615.1 | 11/1985 |

(List continued on next page.)

*Primary Examiner*—Angela D. Sykes
*Assistant Examiner*—Patricia Bianco
(74) *Attorney, Agent, or Firm*—Beth A. Vrioni

(57) ABSTRACT

A cap assembly for a container has a hollow housing with an upper end that receives a fluid transfer device and a lower end that engages a stopper on the container. The housing has an internal cavity open at the upper and lower ends and a radially outwardly extending portion at the lower end. A penetrator is received in the internal cavity. The penetrator has a pointed distal end opposite the stopper and an upper end constructed to be engaged by a fluid transfer device. A cap is constructed the hollow housing. The cap has a closed upper end, an open lower end, a radially outwardly extending portion at the open end, and a circumferential line of weakness connecting the upper and lower ends. A ferrule is over the radially outwardly extending portion of the hollow housing and the radially outwardly extending portion of the cap.

8 Claims, 8 Drawing Sheets

U.S. PATENT DOCUMENTS

| | | | | |
|---|---|---|---|---|
| 3,826,260 A | | 7/1974 | Killinger | |
| 3,872,992 A | | 3/1975 | Larson | |
| 3,940,003 A | | 2/1976 | Larson | |
| 3,977,555 A | * | 8/1976 | Larson | 206/363 |
| 3,995,630 A | | 12/1976 | Van de Veerdonk | |
| 4,048,999 A | | 9/1977 | Kobel | |
| 4,067,440 A | | 1/1978 | Lataix | |
| 4,153,057 A | | 5/1979 | Kobel | |
| 4,296,786 A | * | 10/1981 | Brignola | 141/309 |
| 4,412,623 A | | 11/1983 | Schmidt | |
| 4,493,348 A | | 1/1985 | Lemmons | |
| 4,505,709 A | | 3/1985 | Froning et al. | |
| 4,507,113 A | | 3/1985 | Dunlap | |
| 4,564,054 A | | 1/1986 | Gustavsson | |
| 4,576,211 A | | 3/1986 | Valentini et al. | |
| 4,588,403 A | | 5/1986 | Weiss et al. | |
| 4,619,651 A | | 10/1986 | Kopfer et al. | |
| 4,624,393 A | | 11/1986 | Lopez | |
| 4,662,878 A | | 5/1987 | Lindmayer | |
| 4,673,404 A | | 6/1987 | Gustavsson | |
| 4,675,020 A | | 6/1987 | McPhee | |
| 4,785,868 A | | 11/1988 | Koenig, Jr. | |
| 4,863,453 A | | 9/1989 | Berger et al. | |
| 4,927,423 A | | 5/1990 | Malmborg | |
| 4,932,937 A | | 6/1990 | Gustavsson et al. | |
| 4,951,845 A | | 8/1990 | Pezzoli et al. | |
| 4,982,740 A | | 1/1991 | Broden | |
| 4,995,521 A | | 2/1991 | Von Schuckmann | |
| 5,024,256 A | | 6/1991 | Vadher | |
| 5,035,689 A | | 7/1991 | Schroeder | |
| 5,060,812 A | | 10/1991 | Ogle, II | |
| 5,088,996 A | | 2/1992 | Kopfer et al. | |
| 5,092,840 A | | 3/1992 | Healy | |
| 5,169,385 A | | 12/1992 | Turnbull | |
| 5,215,538 A | | 6/1993 | Larkin | |
| 5,232,029 A | | 8/1993 | Knox et al. | |
| 5,275,299 A | | 1/1994 | Konrad et al. | |
| 5,279,572 A | * | 1/1994 | Hokama | 604/168.01 |
| 5,279,576 A | | 1/1994 | Loo et al. | |
| 5,297,599 A | | 3/1994 | Bucheli | |
| 5,342,319 A | | 8/1994 | Watson et al. | |
| 5,350,372 A | | 9/1994 | Ikeda et al. | |
| 5,358,501 A | | 10/1994 | Meyer | |
| 5,360,413 A | | 11/1994 | Leason et al. | |
| 5,364,386 A | | 11/1994 | Fukuoka et al. | |
| 5,379,907 A | | 1/1995 | Niedospial et al. | |
| 5,397,303 A | | 3/1995 | Sancoff et al. | |
| 5,409,125 A | | 4/1995 | Kimber et al. | |
| 5,411,499 A | | 5/1995 | Dudar et al. | |
| 5,415,374 A | | 5/1995 | Carroll et al. | |
| 5,421,814 A | | 6/1995 | Geary | |
| 5,423,791 A | | 6/1995 | Bartlett | |
| 5,425,465 A | | 6/1995 | Healy | |
| 5,429,256 A | | 7/1995 | Kestenbaum | |
| 5,433,330 A | | 7/1995 | Yatsko et al. | |
| 5,433,703 A | | 7/1995 | Utterberg et al. | |
| 5,437,648 A | | 8/1995 | Graves et al. | |
| 5,441,487 A | | 8/1995 | Vedder | |
| 5,454,409 A | | 10/1995 | McAffer et al. | |
| 5,454,805 A | | 10/1995 | Brony | |
| 5,466,219 A | | 11/1995 | Lynn et al. | |
| 5,470,319 A | | 11/1995 | Mayer | |
| 5,470,327 A | | 11/1995 | Helgren et al. | |
| 5,474,541 A | | 12/1995 | Ritsky et al. | |
| 5,474,544 A | | 12/1995 | Lynn | |
| 5,487,737 A | * | 1/1996 | Meyer | 604/403 |
| 5,501,676 A | | 3/1996 | Niedospial et al. | |
| 5,509,433 A | | 4/1996 | Paradis | |
| 5,514,116 A | | 5/1996 | Vaillancourt et al. | |
| 5,514,117 A | | 5/1996 | Lynn | |
| 5,520,642 A | | 5/1996 | Bigagli et al. | |
| 5,520,665 A | | 5/1996 | Fleetwood | |
| 5,520,666 A | | 5/1996 | Choudhury et al. | |
| 5,573,516 A | | 11/1996 | Tyner | |
| 5,573,520 A | | 11/1996 | Schwartz et al. | |
| 5,573,525 A | | 11/1996 | Watson et al. | |
| 5,573,526 A | | 11/1996 | Hess | |
| 5,616,129 A | | 4/1997 | Mayer | |
| 5,616,130 A | | 4/1997 | Mayer | |
| 5,620,434 A | | 4/1997 | Brony | |
| 5,776,125 A | * | 7/1998 | Dudar et al. | 604/411 |
| 5,785,701 A | * | 7/1998 | Sams et al. | 604/403 |
| 5,879,345 A | * | 3/1999 | Aneas | 215/277 |
| 6,378,576 B2 | * | 4/2002 | Thibault et al. | 141/27 |

FOREIGN PATENT DOCUMENTS

| | | |
|---|---|---|
| DE | 36 18 158 | 12/1987 |
| EP | 0311787 | 9/1988 |
| EP | 0587347 A1 | 8/1993 |
| GB | 1 419 061 | 12/1975 |
| GB | 2 235 135 A | 8/1990 |
| WO | WO 84/04673 | 12/1984 |
| WO | WO 88/01881 | 9/1987 |
| WO | WO 92/11056 | 12/1991 |
| WO | WO 94/03373 | 8/1993 |
| WO | WO 95/0117 | 4/1994 |
| WO | WO 95/33505 | 6/1994 |
| WO | WO 95/14176 | 11/1994 |
| WO | WO 95/03841 | 2/1995 |
| WO | WO 95/31242 | 5/1995 |
| WO | WO 95/35125 | 6/1995 |
| WO | WO 96/13301 | 10/1995 |
| WO | WO 97/00702 | 4/1996 |
| WO | WO 97/10156 | 9/1996 |
| WO | WO 97/39720 | 10/1997 |

* cited by examiner

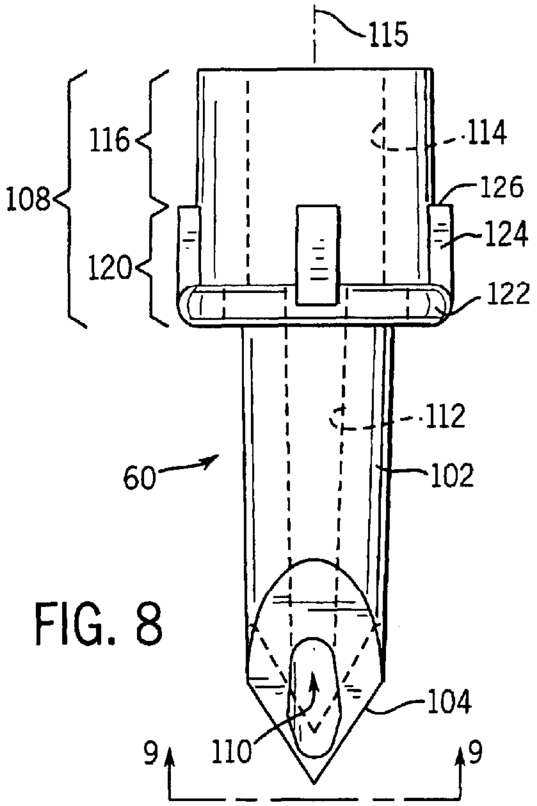
FIG. 8
FIG. 9
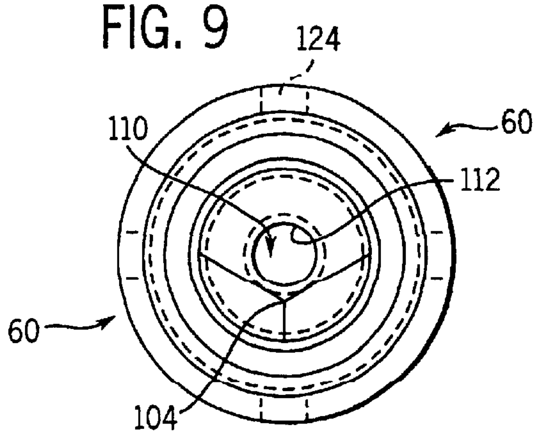
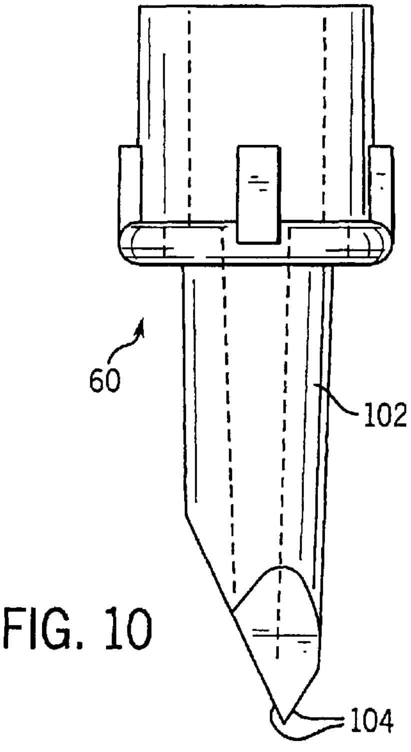
FIG. 10
FIG. 11
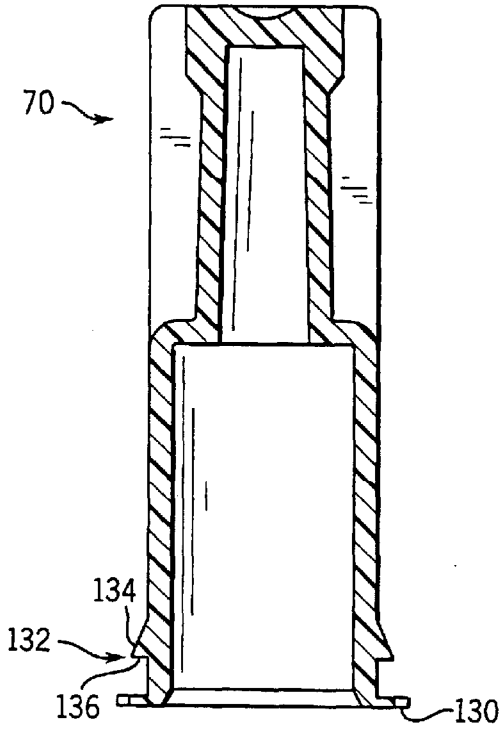

CONTAINER CAP ASSEMBLY HAVING AN ENCLOSED PENETRATOR

CROSS REFERENCE TO RELATED APPLICATION(S)

This is a divisional of U.S. patent application Ser. No. 09/282,959, filed Apr. 1, 1999, which is a divisional of U.S. Ser. No. 08/808,330 now U.S. Pat. No. 5,891,129, filed Feb. 28, 1997.

STATEMENT REGARDING FEDERALLY SPONSORED RESEARCH OR DEVELOPMENT

Not Applicable

REFERENCE TO A MICROFICHE APPENDIX

Not Applicable

TECHNICAL FIELD

The present invention relates to closures for containers, including vials and the like, containing liquid pharmaceutical medicaments or other products. The present invention is directed to a closure for containing and delivering a pharmaceutical product. More particularly, the present invention is directed to a closure that permits the introduction and withdrawal of fluid from a container using an instrument having a blunt luer fitting or connector, such as a luer lock syringe or other fluid transfer device.

BACKGROUND OF THE INVENTION AND TECHNICAL PROBLEMS POSED BY THE PRIOR ART

Many pharmaceutical products are delivered to pharmacies in sealed containers such as glass or plastic vials, glass or plastic bottles, and flexible bags. Such containers can contain a powdered or lyophilized formulation of a pharmaceutical product that must be reconstituted prior to administration to a patient. In addition, such containers can contain a solution or suspension formulation of a pharmaceutical product that can be withdrawn from the container and administered directly to a patient, for example, by parenteral administration.

Most pharmaceutical vials are seated by a pierceable stopper which is press-fit into the mouth of the vial to thereby isolate the contents of the vial from the vial's external environment. In order to access the pharmaceutical product within the vial, it is necessary either to pierce the stopper or to remove the stopper from the vial. However, removal of the stopper results in exposure of the pharmaceutical product to the external environment, thereby compromising the sterility and/or stability of the pharmaceutical product within the vial. For this reason, it often is preferable to access the pharmaceutical product by piercing the stopper.

A conventional syringe can be used to add a diluent to the vial and/or to withdraw liquid from the vial. The syringe has a hollow cannula or needle which is pushed through the stopper and into communication with the liquid. The syringe plunger can be depressed to dispense a diluent into the vial or pulled outwardly to draw liquid from the vial into the syringe.

The piercing of vial stoppers typically has been achieved through the use of sharp, small-bored needles. Standard hypodermic syringe needles are particularly useful for this purpose because they allow the pharmaceutical product to be aseptically withdrawn from the vial and parenterally administered directly to a patient using a single device, thereby minimizing risk of contamination of the pharmaceutical product.

While the above-described conventional system has long been used with satisfactory results, it is not without disadvantages. A fundamental disadvantage is the necessity of using a syringe with a sharp needle. This exposes the medical professional to the possibility of being accidently pricked by the syringe needle. In addition to the undesirable injury resulting from such an accidental needle prick, there may be a risk of contamination of the needle by the medical professional. If the medical professional violates safe procedures and continues to use a contaminated syringe to withdraw the liquid medicament from the vial and administer it to a patient, there is a risk of transmitting the contaminant to the patient.

In addition, if the syringe needle is used to inject the liquid medicament into a patient, there is a danger that the medical professional could accidentally be pricked by the needle following the injection of the patient. This could expose the medical professional to contamination from the patient, especially pathogens carried in blood.

In many cases it is necessary to clean the outer surface of the vial stopper prior to piercing in order to reduce the risk of infection to the patient. This requires the medical professional to perform two distinct steps in order to withdraw the pharmaceutical product from the vial.

It would be desirable to provide an improved closure system that would permit withdrawal of liquid medicament from a closed vial without requiring the use of a syringe having an exposed, sharp needle.

It would also be advantageous to provide such an improved system which can provide simple and rapid access to the liquid medicament contained within the vial.

Preferably, such an improved system should accommodate current product designs and manufacturing techniques to as great an extent as possible. Also, it would be desirable if such an improved system could be employed with conventional, luer lock syringes. Further, such an improved system should preferably accommodate the design of components that can be manufactured at very low cost, with mass production techniques, with low product reject rates, and with high reliability.

Additionally, it would be desirable if the improved design could be easily operated to establish a reliable communication between the syringe or other luer lock transfer device and the liquid medicament in the vial in a way that would minimize the possibility of interrupted withdrawal flow or reduced withdrawal flow.

Further, it would be beneficial if such an improved design could provide evidence of tampering.

The present invention provides an improved container stopper penetrator, a novel process for making a penetrator, and an improved container cap assembly with an integral stopper penetrator which can accommodate designs having the above-discussed benefits and features.

SUMMARY OF THE INVENTION

According to one aspect of the present invention, a piercing member or penetrator is provided for being disposed in a cavity of a housing over a stopper that occludes the mouth of a container. The penetrator is adapted for piercing or penetrating the stopper upon movement of the penetrator into the stopper.

In one embodiment, a penetrator is stamped from sheet metal. The sheet metal is formed to define a shank having a length, a groove extending along its length, and a pointed distal end. The sheet metal is also formed to define a bearing plate extending from the shank at an end opposite the pointed distal end. In a preferred embodiment, the sheet metal is further formed to provide at least a first guide wall extending from the shank intermediate the pointed distal end and the bearing plate.

According to a method aspect of the invention, the metal penetrator is fabricated in a number of processing steps. A plurality of progressive die stations are provided, and each die station comprises an associated complementary punch and die. A planar strip of sheet metal is indexed to incrementally advance progressively between the punches and dies. Each die station is operated after each incremental advancement of the sheet metal strip to effect relative movement between the associated punch and die so as to sever and separate regions of the strip. This process defines a bearing plate portion and a pointed shank portion of the penetrator. Preferably, an extending guide wall portion is also formed.

In a preferred form of the method, the die stations are operated to define part of the periphery of at least one of the stamped metal portions at one of the stations and to define another part of the periphery of that portion at another, downstream station. Further, some of the stations also effect deformation of the metal strip by bending the shank portion into a configuration defining a convex surface and a concave surface oriented along a longitudinal axis. Other stations effect deformation of the metal strip by bending the bearing plate portion out of the plane of the strip. Preferably, a guide wall portion is also bent into a configuration extending out of the plane of the strip to define a guide surface that is generally parallel to the longitudinal axis, According to another aspect of the invention, another embodiment of a penetrator is molded from a plastic material as a unitary structure. The molded penetrator includes a shank molded from plastic material, and the shank has a distal end defining a point. The penetrator also has a hub at the end of the shank opposite the shank distal end. The hub is molded from the plastic material so that it is unitary with the shank, and the hub defines an upper end of the penetrator. The hub and shank together define a transfer passage extending from the upper end to the pointed distal end. The transfer passage opens from the hub at the upper end and opens from the shank at the pointed distal end.

The invention includes a third embodiment of a penetrator for a container stopper. The third embodiment of the penetrator comprises a hollow needle having a base end and a pointed distal end. The penetrator further includes a hub of plastic material molded around the needle base end. In a preferred form of the third embodiment of the penetrator, the hub has an upper, smaller diameter cylindrical portion and a lower, larger diameter cylindrical portion.

According to yet another aspect of the present invention, a cap assembly is provided for a container which has an upper portion defining a mouth occluded by a stopper having a top end. The cap assembly includes a hollow housing. The housing defines a lower end adapted to be mounted on the container, an upper end, and an internal cavity opening at the housing upper and at the housing lower end.

The cap assembly further includes a penetrator that is disposed in the housing cavity. The penetrator has a lower, pointed, distal end and has an upper end adapted to be engaged by the distal end of the transfer device male member when the transfer device is moved into the housing. The penetrator defines a fluid transfer passage extending from the penetrator upper end to the penetrator pointed distal end. The penetrator is moveable between a retracted position completely within the housing cavity and an extended position in which the penetrator projects from the housing cavity at the housing lower end.

The cap assembly also includes a removable cap disposed on, and sealingly engaged with, the exterior of the housing so as to seal the housing cavity at the housing upper end.

Finally, the cap assembly includes a ferrule disposed over a radially outwardly extending flange of the lower end of the housing. The ferrule has a skirt adapted to be received on the container around both the stopper and the upper portion of the container. The skirt is preferably metal so that it can be crimped into engagement with the upper portion of the container to hold the ferrule and housing to the container with the penetrator and cap carried by the housing.

The cap assembly provides a sterile protective covering for the container stopper.

The cap assembly can also include tamper-evident features.

The cap assembly can be manufactured reliably and at low cost.

Importantly, the cap assembly readily connects to a conventional male luer. The penetrator within the cap assembly readily pierces the vial stopper, but the distal, piercing end of the penetrator is never exposed. This eliminates or minimizes the likelihood that a medical professional will be accidently pricked by a sharp, pointed component when handling the cap assembly and withdrawing a medicament from the container.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIG. 8 is a front elevational view of the penetrator of the cap assembly shown in FIG. 4;

FIG. 9 is a bottom, plan view taken along the plane 9—9 in FIG. 8;

FIG. 10 is a side elevational view of the penetrator shown in FIGS. 8 and 9;

FIG. 11 is a cross-sectional view of the overcap of the assembly illustrated in FIG. 4;

DESCRIPTION OF THE PREFERRED EMBODIMENT

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the components of this invention are described in the positions depicted in the accompanying drawings, and terms such as upper, lower, horizontal, etc., are used with reference to this position. It will be understood, however, that the components of this invention may be manufactured, stored, transported, used, and sold in an orientation other than the position described.

Figures illustrating the components show some mechanical elements that are known and that will be recognized by one skilled in the art. The detailed descriptions of such known elements are not necessary to an understanding of the invention, and accordingly, are herein presented only to the degree necessary to facilitate an understanding of the novel features of the present invention.

The components of this invention are intended to be used with certain other conventional instruments and/or components the details of which, although not fully illustrated or described, will be apparent to those having skill in the art and an understanding of the necessary functions of such components.

One aspect of the invention facilitates rapid and safe access to the contents stored within a sealed container. The invention is especially suitable for use with a container such as a glass or plastic vial containing a pharmaceutical product or medicament. However, it will be appreciated that other applications of the present invention are feasible, including, but not limited, applications in connection with parenteral tube sets. The pharmaceutical product may be in liquid (solution or suspension) form or in a solid form, e.g., powdered or lyophilized. The invention is especially useful with a conventional vial which is normally sealed with a rubber stopper and which is conventionally designed to be pierced by a hollow needle or cannula of a hypodermic syringe so that the contents of the vial can be diluted/reconstituted with the syringe contents and/or so that the contents of the vial can be withdrawn into the syringe for subsequent discharge into another container system or for direct administration to a patient.

Figure 1:
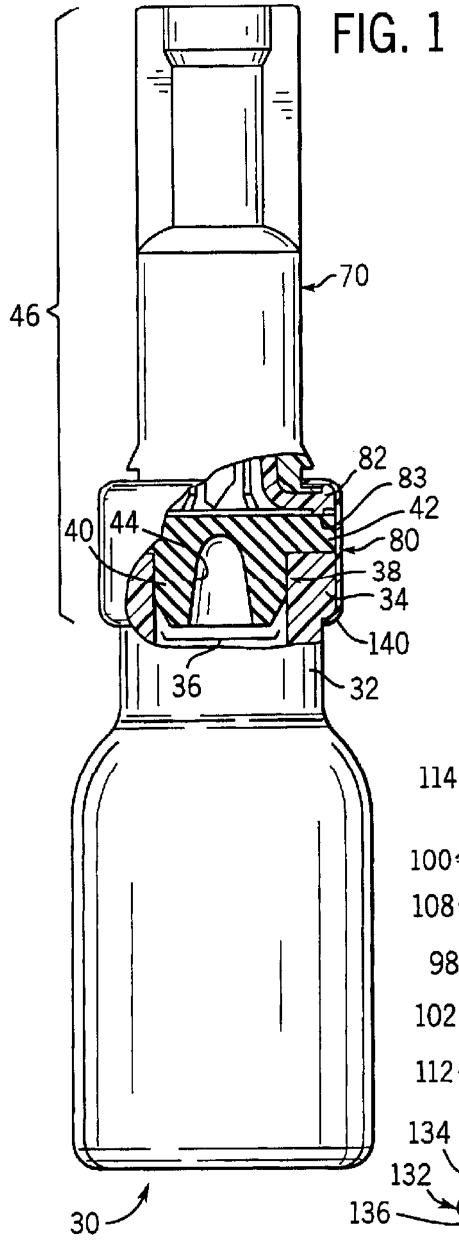
FIG. 1 is a side elevational view of a container cap assembly of the present invention showing it installed on a vial.

FIG. 1 illustrates a container such as a conventional glass or plastic vial 30 having a cylindrical neck 32 terminating in a slightly larger diameter annular flange 34 which defines an opening or mouth 36 of the container.

The mouth of the vial 30 contains an internal, removable, resilient seal, plug or stopper 38. The stopper 38 is typically made from rubber or other suitable elastomeric material. The stopper 38 includes a central, generally annular, plug portion 40 and an enlarged diameter head portion 42. The head portion 42 functions as a support flange and is normally disposed on the top end surface of the container neck flange 34. The stopper annular plug portion defines an internal recess 44 which opens downwardly toward the container contents.

The stopper 38 prevents the discharge, or removal, of the contents from the vial 30 unless and until the stopper is either removed or penetrated. In a preferred embodiment, stopper 38 does not define channels or pores therethrough, i.e., stopper 38 is not "pre-pierced". However, the cap assembly of the present invention can be used with stoppers that define one or more channels or pores therethrough. One aspect of the present invention provides a special system for penetrating the stopper 38 to gain access to the contents of the vial 30 as explained in detail hereinafter.

The annular plug portion 40 of the conventional stopper 38 preferably has an exterior diameter which is slightly larger than the interior diameter of the mouth 36 of the container neck 32. Typically, the stopper annular body 40 is received in the container mouth 36 in a radially, inwardly compressed condition and is retained within the container mouth 36 by frictional engagement established by the outward force of the stopper annular body portion 40 on the vial neck 32 owing to the resiliency of the stopper material.

One aspect of the present invention provides a special cap assembly 46 which has a number of functions. The cap assembly 46 covers the top of the stopper 38 as well as an upper portion of the container neck 32 to protect the stopper 38 and upper portion of the container as well as to provide a barrier to contaminant ingress.

The cap assembly 46 also functions as an additional mechanism for holding the stopper 38 and container 30 together in a sealed relationship.

Further, the cap assembly 46 permits rapid connection of the container 30 to a luer-type fluid transfer device, such as a conventional luer lock syringe (described in detail hereinafter).

Additionally, the cap assembly 46 functions to contain a pointed piercing member or penetrator and to accommodate penetration of the stopper 38 with the penetrator in a way that does not expose the medical professional or patient to a pointed or sharp component. Other advantages and features of the cap assembly 46, as well as the detailed construction, method of fabrication, and method of use, are described in detail hereinafter.

The vial 30 can be a pharmaceutical vial of known construction. However, it will be appreciated that closure assembly 46 can be adapted to seal a wide variety of containers and devices for containing pharmaceutical or non-pharmaceutical products. The depiction herein of a pharmaceutical vial 30 is not intended to be limiting, but instead represents one useful application of the system of the present invention. The container also can be a plastic or glass bottle, a flexible bag of known construction, or a parenteral or enteral tube set. For the purposes of this disclosure, all references to the terms "container" and "vial" are intended to include, inter alia, vials, bottles, flexible containers, parenteral or enteral tube sets, and equivalents thereof.

The vial 30 is filled with product, and the stopper 38 is inserted in the mouth of the vial 30 in a separate conventional or special process, the details of which form no part of the present invention. The cap assembly 46 is initially manufactured as an assembly separate from the vial 30 and stopper 38. After manufacture of the cap assembly 46, and prior to its installation over the stopper 38 on the filled container 30, the cap assembly 46 has a configuration as illustrated in cross section in FIG. 2.

Figure 3:
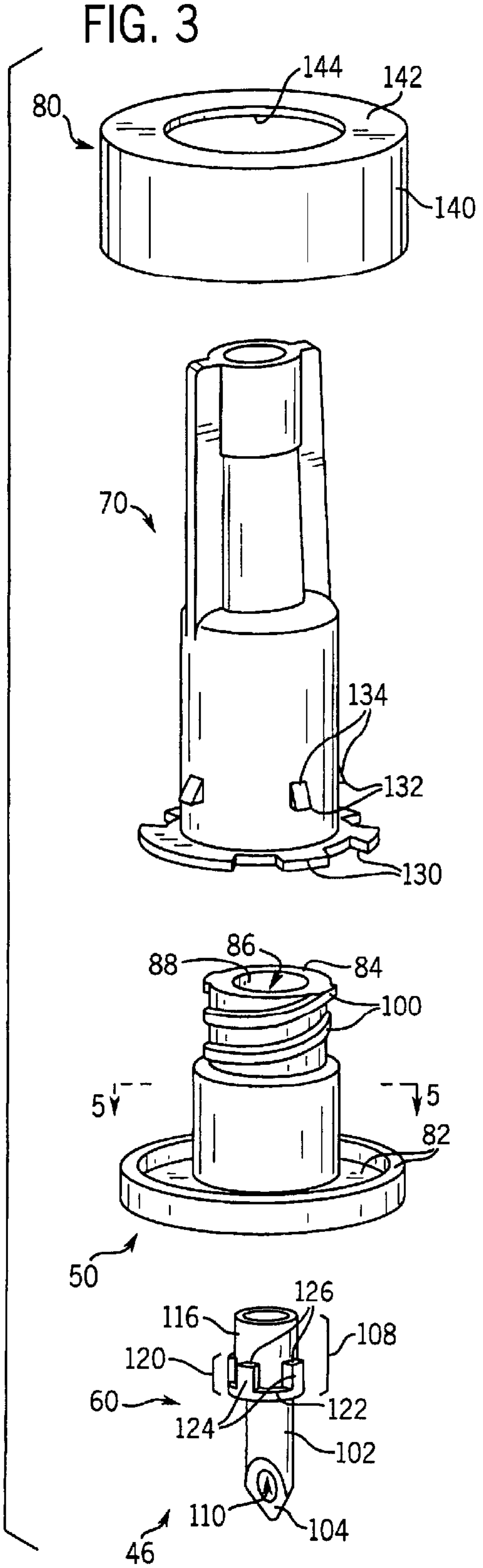
FIG. 3 is an exploded, perspective view of the components of the cap assembly illustrated in FIG. 2.
Figure 4:
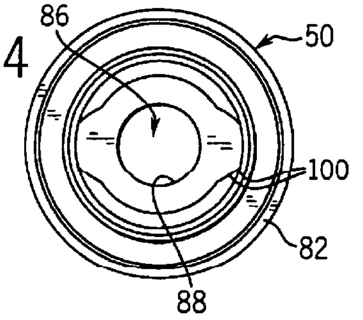
FIG. 4 is a top view of the housing in the cap assembly shown in FIG. 3.
Figure 5:
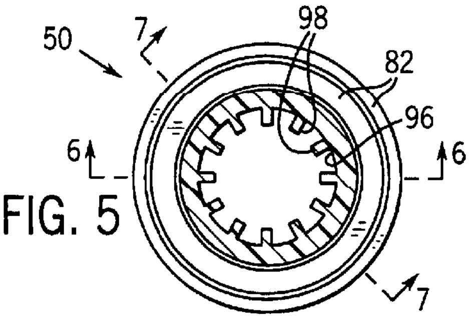
FIG. 5 is a cross-sectional view taken generally along the plane 5—5 in FIG. 3.

The separate components of the cap assembly 46 are illustrated in the perspective view in FIG. 3. The cap assembly 46 includes a hollow housing 50 in which is slidably disposed a penetrator 60. An overcap or cap 70 is provided for covering and sealing the top portion of the housing 50. The housing 50 and penetrator 60 are preferably constructed such that they are held together by frictional forces therebetween. Ferrule 80 is provided to retain radially outwardly extending lower end 82 of housing 50 on vial 30. Ferrule is preferably constructed of a metal material, but may be constructed of other known materials without departing from the scope of the present invention. When the assembly 46 is mounted to the top of the container 30, the lower end 82 of the housing 50 rests either on vial 30 or on the top surface of stopper 38, dependent upon the configuration of stopper 38. A bottom peripheral portion of the metal ferrule 80 is crimped about the lower edge of the flange 34 of the container 30 as shown in FIG. 1.

Figure 6:
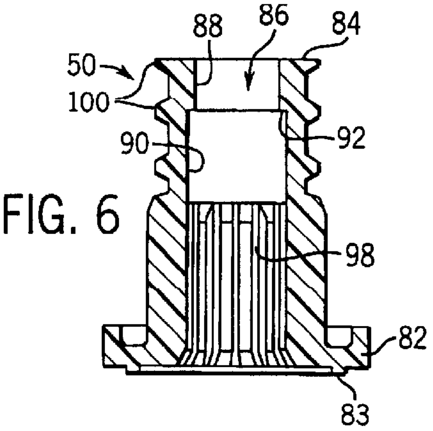
FIG. 6 is a cross-sectional view taken generally along the plane 6—6 in FIG. 5.
Figure 7:
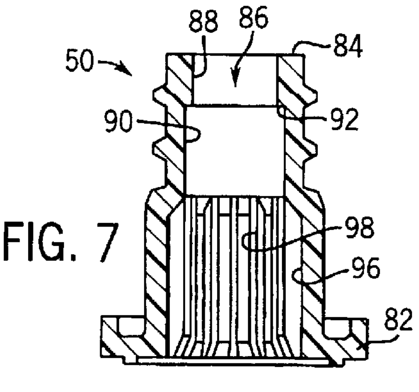
FIG. 7 is a cross-sectional view taken generally along the plane 7—7 in FIG. 5.

As shown in FIGS. 1 and 6, the housing lower end 82 may include a downwardly extending element such as annular seal ring 83 for engaging a top surface of the stopper 38 and effecting a leak-tight seal when the two components are held in clamping engagement by the crimped, metal ferrule 80.

As shown in FIGS. 3–7, the housing 50 has an upper end 84 which is open to an internal cavity 86. The internal cavity 86 extends through the housing 50 and opens at the lower end 82. The housing cavity 86 defines an upper bore 88 which is open at the housing upper end 84. The upper bore 88 preferably is frustoconical to define a luer-compatible taper (i.e., a 1.7° side taper or 3.4° included conical angle). In the preferred embodiment of the present invention, upper bore 88 is shorter in length than a conventional luer, thereby ensuring that a luer can be inserted into upper bore 88 to an extent great enough to impart the requisite degree of travel to penetrator 60, as explained in greater detail below.

The cavity 86 also includes a lower, cylindrical bore 90 that communicates with the upper bore 88. The lower, cylindrical bore 90 opens at the housing lower end 82. The upper bore 88 has a diameter less than the diameter of the lower, cylindrical bore 90. This defines an annular shoulder 92 (FIGS. 6 and 7) adjacent the upper bore 88 within the lower, cylindrical bore 90. The bore 90 may have a small draft angle, but is cylindrical in the preferred embodiment of the present invention.

The lower, cylindrical bore 90 includes a plurality of circumferentially spaced, interior channels 96 (FIG. 5) defined between ribs 98. The housing 50 is preferably molded as a unitary structure from a plastic material such as polypropylene, and the vertical inner edges of each rib 98 are preferably provided with a draft angle (e.g., 2°) to assist in separation of the housing 90 from the mold parts. The ribs 98 function to guide the penetrator 60 as it moves downwardly to penetrate the vial stopper 38 as described in detail hereinafter. In the preferred embodiment of the present invention, ribs 98 do not extend inwardly any further than the wall of lower bore 90.

In order to make the cap assembly of the present invention accessible by means of a locking luer, the upper exterior portion of the housing 50 preferably defines a laterally projecting formation, such as a conventional luer lock dual lead helical thread formation 100 (FIGS. 3 and 6). The laterally projecting thread formation 100 is designed for threadingly engaging a mating thread system on an annular skirt of a luer lock-type fluid transfer device, such as a luer lock syringe (as described in detail hereinafter).

The first embodiment of the penetrator 60 (FIGS. 8–11) which is adapted for being received in the housing 50 is a unitary structure molded from plastic material. The penetrator 60 has a shank 102 with a point defining a pointed distal end 104. The penetrator 60 has a hub 108 (FIG. 8) at the end of the shank 102 opposite the pointed distal end 104, and the hub 108 defines the upper end of the penetrator 60.

Figure 2:
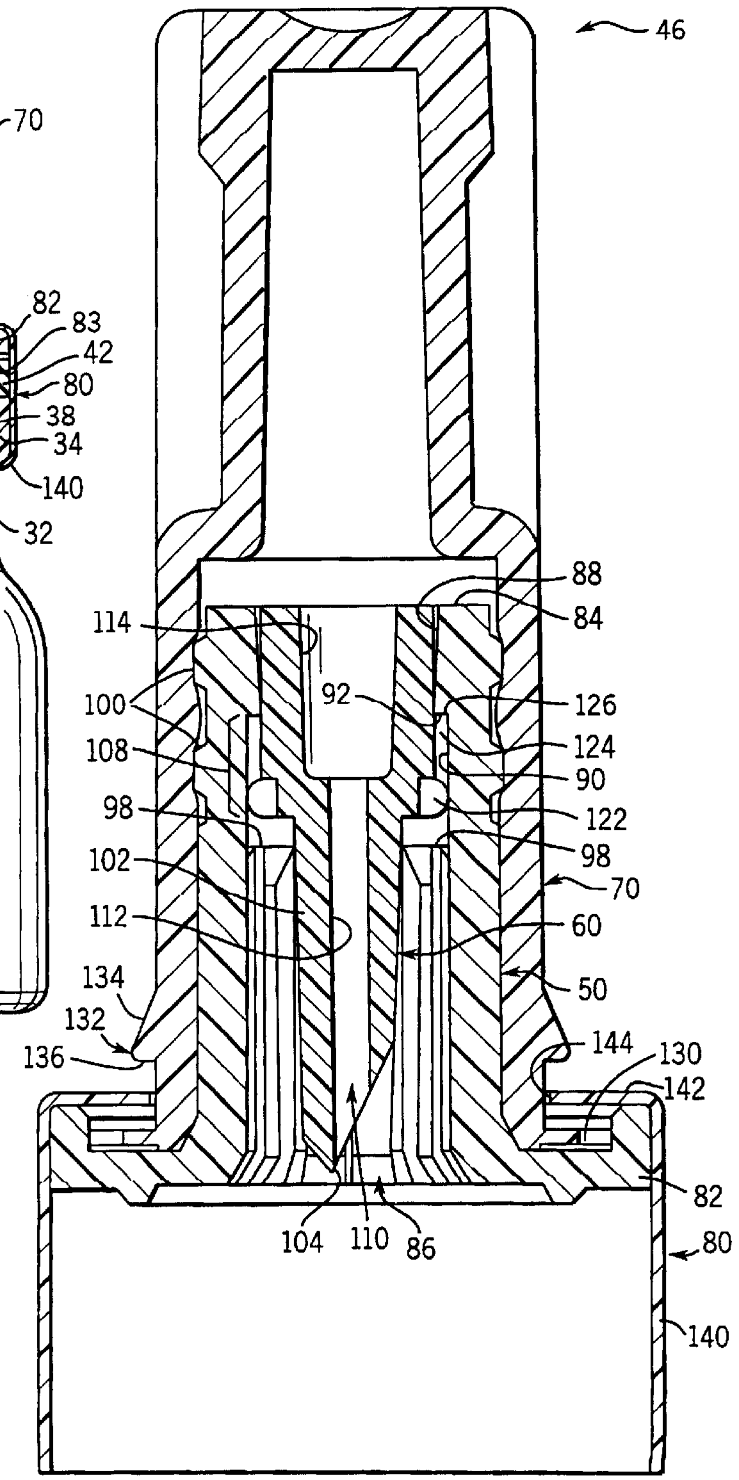
FIG. 2 is a cross-sectional view of the cap assembly prior to installation on the vial.

The penetrator 60 defines a transfer passage 110 which extends from the pointed distal end 104 through the shank 102 and through the hub 108. As illustrated in FIG. 2, the transfer passage 110 comprises a lower, cylindrical bore 112 communicating with an upper, cylindrical bore 114. The upper, cylindrical bore 114 has a diameter which is larger than the diameter of the lower, cylindrical bore 112. The hub 108 may be characterized as defining a central, longitudinal axis 115 (FIG. 8), and the transfer passage upper bore 114 and lower bore 112 are axially aligned on the longitudinal axis 115.

The hub 108 of the penetrator 60 has a smaller diameter, upper, cylindrical portion 116 (FIG. 8) and a larger diameter lower portion 120. Both the upper portion 116 and lower portion 120 are axially aligned along the longitudinal axis 115 of the penetrator 60. The larger diameter lower portion 120 includes an annular bead or rib 122 (FIGS. 2 and 3) which has a diameter which defines the larger diameter of the lower portion 120 of the hub 108. The hub larger diameter lower portion 120 also includes a plurality of circumferentially spaced ribs 124. In the preferred embodiment of the present invention depicted in the accompanying figures, four circumferentially spaced ribs 124 extend axially from the bead 122 parallel to the longitudinal axis 115 of the penetrator 60. The longitudinal lengths of the ribs 124 all terminate axially at the same distance from the bead 122 so as to define an abutment end 126 at the top end of each rib 124. Each rib 124 also extends radially outwardly and terminates radially on the diameter of the hub lower portion 120 as established by the outer diameter of the annular bead 122.

As shown in FIG. 2, the ribs 124 of the lower portion of the hub 108 are received within the larger diameter, lower cylindrical bore 90 of the housing 50. The abutment end 126 of each rib 124 can engage the internal shoulder 92 of the housing 50 to establish an uppermost elevational position of the penetrator 60 within the housing 50. In a preferred embodiment, the outer diameter of ring 122 is slightly larger than the nominal diameter of the housing lower bore 90. Specifically, in one presently contemplated embodiment, the exterior diameter of the ring 122 is up to 0.004 inches greater than the nominal diameter of the housing receiving bore 90. This establishes a slight interference fit so that the penetrator 60 can be initially maintained generally in the highest elevation shown in FIG. 2 within the housing 50. In this position, the pointed distal end 104 is retracted somewhat inwardly (upwardly) from the opening of the cavity 86 at the bottom end of the housing 50.

In some manufacturing sequences, the cap assembly 46 may be stored separately until it is mounted on the vial 30. The above-described retention features prevent the penetrator 60 from slipping out during such storage as well as during the process of mounting the cap assembly 46 on the vial 30.

During the initial assembly of the components, the penetrator 60 must be forced upwardly into the housing cavity 86 with sufficient force to slightly compress the bead 122 radially inwardly and/or to temporarily expand the housing 50 radially outwardly. Then the penetrator 60 can be moved further inwardly (upwardly) to the elevated position wherein the penetrator bead 122 is above the upper ends of the housing ribs 98. Preferably, the penetrator 60 is fully inserted to the elevated position illustrated in FIG. 2 wherein the abutment ends 126 of the penetrator ribs 124 engage the housing shoulder 92.

When the penetrator 60 is subsequently moved downwardly to pierce the container stopper 38 as described in detail hereinafter, the hub lower portion 120, including the exterior surfaces of the ribs 124, function as a guide wall for guiding the downward movement of the penetrator 60 through the housing cavity 86, including along the housing bore 90 and along the inwardly projecting guide ribs 98.

The overcap 70 is removable from the assembly 46. The overcap 70 has an elongated, tubular configuration with a closed top end and an open bottom end. The bottom end includes a plurality of flexible tabs 130 (FIG. 3) which extend radially over a portion of the housing lower end 82 under the ferrule 80 when the components are assembled as shown in FIG. 2. The overcap 70 also preferably includes a plurality of circumferentially spaced retention tabs 132. Each retention tab 132 has a downwardly and outwardly angled camming surface 134 and has a downwardly facing retention shoulder 136.

The metal ferrule 80 is disposed over the radially outwardly extending lower end 82 of the housing 50. The ferrule 80 has a skirt 140 adapted to be received on the container 30 around both the stopper 38 and an upper portion of the container 30. A lower portion of the skirt 140 can be crimped into engagement with the lower portion of the container flange 34, as depicted in FIG. 1.

The ferrule 80 also includes a radially inwardly extending, annular deck 142 defining a receiving aperture 144 (FIGS. 2 and 3). The receiving aperture 144 receives the subassembly of the penetrator 60, housing 50, and overcap 70. During assembly of the ferrule over the overcap 70, the inner edge of the annular deck 142 (at the aperture 144) engages the camming surfaces 134 on the retention lugs 132. This temporarily deflects the annular deck 142 outwardly slightly and/or deflects the overcap 70 inwardly until the deck 142 moves downwardly past the retention shoulders 136 of the lugs 132. It will be appreciated that lugs 132 impair the movement of ferrule 80 relative to overcap 70 during placement of the cap assembly on a container. That is, after the ferrule 80 is assembled with the other components as shown in FIG. 2, the ferrule 80 is able to move upwardly slightly until it engages the retention shoulders 136 on the retention lugs 132. However, the metal ferrule 80 cannot move upwardly beyond the retention lugs 132.

The cap assembly 46 can be assembled either manually or, preferably, by automatic assembly machinery (the details of which form no part of the present invention). The completed cap assembly 46 can then be immediately mounted on a container 30 or can be stored for later mounting on a container 30. The components of the assembly 46 remain in the assembled condition with the penetrator 60 fully retracted within the housing 50.

Figure 12:
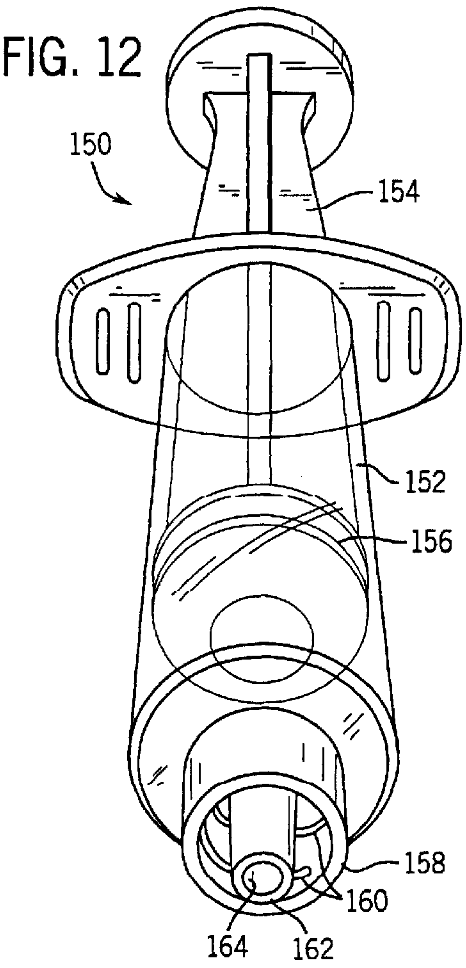
FIG. 12 is a perspective view of a conventional luer lock type syringe.

After the assembly 46 is mounted and crimped to a container 30 as shown in FIG. 1, the cap assembly 46 may be readily connected to a luer-type fluid transfer device, such as a luer lock syringe 150 as shown in FIG. 12. Use of the present invention will now be described in connection with a luer lock syringe 150. However, it will be appreciated that this description is for exemplary purposes only and that use of the present invention is not limited to a luer lock syringe.

The luer lock syringe 150 includes a barrel 152 and a telescopically received plunger 154. The distal end of the plunger 154 includes a conventional piston or grommet 156 sealingly engaged with the interior cylindrical surface of the barrel 152.

The distal end of the syringe 150 has a conventional annular skirt 158 which is internally threaded with a conventional luer lock dual lead helical thread system 160. A conventional male cannula 162 projects from the distal end of the barrel 152 within the annular skirt 158. The cannula 162 has a conventional exterior taper which reduces the exterior diameter of the cannula 162 to a minimum at the bottom, distal end of the cannula 162. The cannula 162 defines a bore 164 which is in communication with the interior volume of the syringe barrel 152 below the syringe plunger piston 156.

Figure 13:
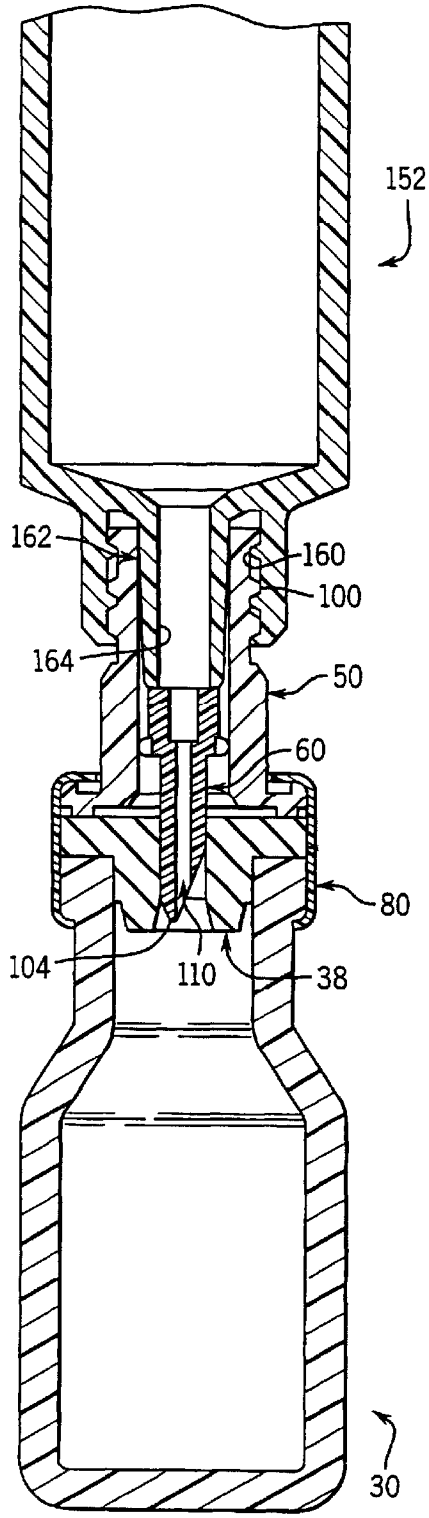
FIG. 13 is a view similar to FIG. 2, but FIG. 13 shows the syringe of FIG. 12 attached to the housing of the cap assembly after removal of the overcap and shows the penetrator in the fully extended, lowered, position penetrating the stopper in the mouth of the vial.

As shown in FIG. 13, the syringe 150 can be coupled with the container 30. To this end, the overcap 70 (FIG. 1) must first be removed. This is effected by manually grasping the upper end of the overcap 70 and pulling it upwardly away from the container 30. The tabs 130 around the bottom end of the overcap 70 are temporarily deformed downwardly and pass through the ferrule aperture 144 as the cap 70 is pulled upwardly.

Once the overcap 70 is free of the metal ferrule 80, the overcap 70 cannot readily be placed back into position because the cap tabs 130 cannot easily be repositioned under the ferrule annular deck 142. Thus, once the overcap 70 is removed, it cannot be readily placed back on the assembly in the properly mounted condition. Rather, the overcap 70, once removed, will most likely be placed only loosely over the top of the housing 50, and the cap tabs 130 at the bottom end of the overcap 70 will remain outside of, and on top of, the ferrule annular deck 142. This will provide a visual indication that the overcap 70 has been removed from its original, properly mounted position. This provides the assembly 46 with a tamper-evident feature.

After the overcap 70 is removed, the syringe 150 is threadingly engaged with the luer lock thread system 100 on the housing 50. The syringe thread system 160 engages the housing thread system 100. As relative rotation is effected between the syringe 150 and the container 30, the male member 162 of the syringe 152 moves downwardly against the upper end of the penetrator 60. This pushes the penetrator 60 downwardly along the internal cavity in the housing 50.

As the penetrator 60 moves downwardly within the housing 50, the penetrator pointed distal end 104 pierces the stopper 38 and establishes communication between the interior of the container 30 and the penetrator fluid transfer passage 110. As shown in FIG. 13, the upper end of the penetrator fluid transfer passage 110 is in communication with, and is generally axially aligned with, the bore 164 in the syringe cannula 162. The syringe plunger 154 (FIG. 12) can then be moved outwardly within the syringe barrel 152 to reduce the pressure within the syringe and to draw the liquid from the container into the syringe. Alternatively, the syringe 152 can be initially employed to dispense a diluent or another medicament into the container. Subsequently, the mixed contents in the container 30 can be withdrawn with the syringe 150 or with a similar, but different syringe 150.

It will be appreciated that the design of the housing bore 90 and guide ribs 98, and the design of the penetrator hub guide ribs 124, facilitate the downward movement of the penetrator 60 and prevent the penetrator from cocking.

The cap assembly 46 can advantageously be mounted to existing, conventional packages comprising a conventional vial 30 and conventional rubber stopper 38.

The cap 46 is readily connected to a conventional standard luer lock syringe designed according to the conventional ISO Standard 594.

The medical professional can use the cap 46, along with a standard luer lock syringe, to readily gain access to the contents of a vial 30 without the need for a sharp needle. Even the molded plastic penetrator 60 is entirely contained within the cap assembly 46, and the pointed distal end 104 is never exposed where it could be contacted by medical personnel.

The cap assembly 46 has the advantage of not requiring the medical professional to swab the top of the stopper 38 or parts of the cap assembly 46 with alcohol or similar anti-microbial agent. Overcap 70 preferably provides a sterile barrier between the interior of cap 46 and the external environment of overcap 70. The interior of cap 46 can be sterilized using known processes that form no part of the present invention.

The cap assembly 46 accommodates efficient manufacturing processes because the components can be assembled into a single unit or assembly by snap-fitting the components together and/or interference fitting the components together. The completed assembly 46 can be sterilized prior to, during, or after the final mounting of assembly 46 on the vial 30.

The cap assembly 46 can be readily designed for industry standard size vial closures, such as 13 mm, 20 mm, and 28 mm. The assembly 46 is suitable for use with glass vials or plastic vials as well as flexible bags.

It will also be appreciated that the luer-type connection configuration of the cap assembly housing 50 may be employed with fluid transfer devices other than a luer lock syringe as discussed herein. For example, the upper end of the housing 50 of the cap assembly 46 may be connected to a suitable luer-type instrument that is part of another device or that is attached to a length of flexible tubing.

Figure 14:
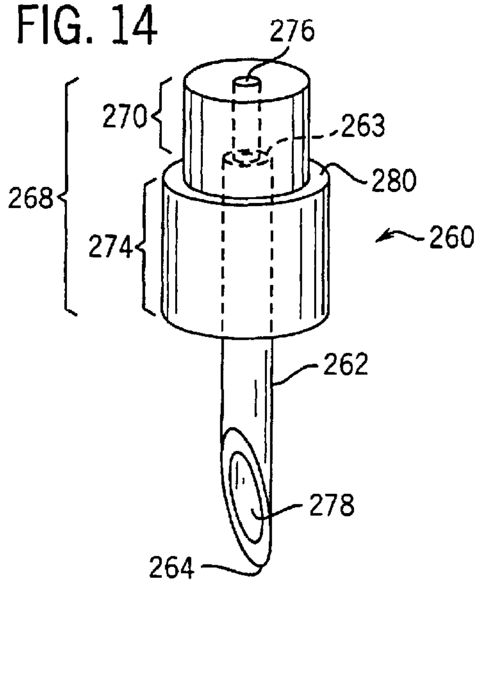
FIG. 14 is a perspective view of a second embodiment of a penetrator that employs a needle and that may be used in the cap assembly.

FIG. 14 illustrates a second embodiment of a penetrator 260 which may be used in the cap assembly 46 in place of the first embodiment of the penetrator 60 described above. The penetrator 260 includes a hollow needle 262 having a base end 263 and a point 264 opposite the base end 263 so as to define a pointed distal end. The penetrator 260 also includes a hub 268 molded from a plastic material around an upper portion of the hollow needle 262 so as to encapsulate the base 263.

The hub 268 has an upper, smaller diameter cylindrical portion 270 and a lower, larger diameter cylindrical portion 274. The upper cylindrical portion defines a bore 276 communicating with the upper end of a bore 278 defined by the hollow needle 262.

The larger diameter cylindrical portion 272 of the hub 268 defines an annular shoulder 280 around the smaller diameter cylindrical portion 270.

The penetrator 260 may be disposed within a cap assembly housing in substantially the same manner as the first embodiment of the penetrator 60 is disposed in the housing 50. To this end, and with reference to FIG. 2, the second embodiment of the penetrator 260 is adapted to be disposed within the housing 50 so that the needle 260 extends downwardly in the same manner as does the shank 102 of the of the first embodiment penetrator 60. The second embodiment penetrator hub 268 is adapted to be disposed within the housing upper bore 88 and within the housing lower bore 90 in substantially the same way as the hub of the first penetrator 60 as shown in FIG. 2. In particular, the smaller cylindrical portion 270 of the second embodiment penetrator 260 is adapted to be disposed within the housing upper bore 88, and the larger, lower cylindrical portion 274 of the hub of the second embodiment penetrator 260 is designed to be disposed within the lower bore 90 of the housing 50. The second penetrator annular shoulder 280 is designed to engage the downwardly facing shoulder 92 of the housing 50, and this establishes the uppermost position of the penetrator 260.

The overcap 70 (FIG. 3) and metal ferrule 80 (FIG. 3) are assembled over the housing 50 with the penetrator 260 contained therein in the same manner as discussed above with respect to the first embodiment of the cap assembly 46 containing the penetrator 60 illustrated in FIGS. 1–3. The cap assembly 46 is then mounted on, and crimped to, the container 30 as previously described.

In use, after the overcap 70 (FIG. 1) is removed, the syringe 150 is attached to the housing 50. The second embodiment of the penetrator 260 is adapted to be engaged by the cannula 162 (FIG. 12) of the syringe 150 when the syringe is threadingly engaged with the housing 50 (as shown in FIG. 13). The second embodiment of the penetrator 260 is designed to be forced downwardly when the syringe 150 moves downwardly as the syringe is threadingly coupled to the cap assembly housing 50. The second embodiment of the penetrator 260 is designed to pierce the stopper 38 so as to establish communication between the syringe 150 and the interior of the container 30.

Figure 15:
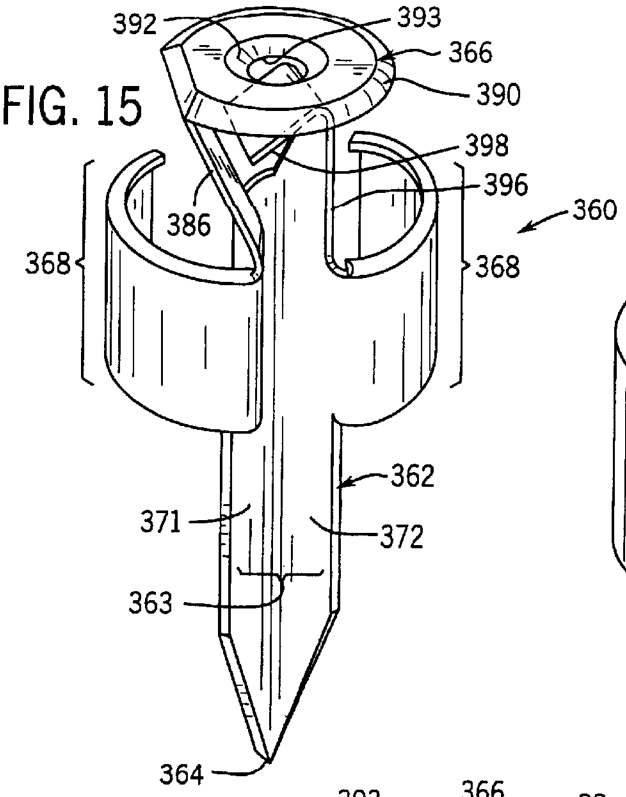
FIG. 15 is a front, perspective view of a third embodiment of a penetrator that is stamped from sheet metal and that may be used in the cap assembly.
Figure 27:
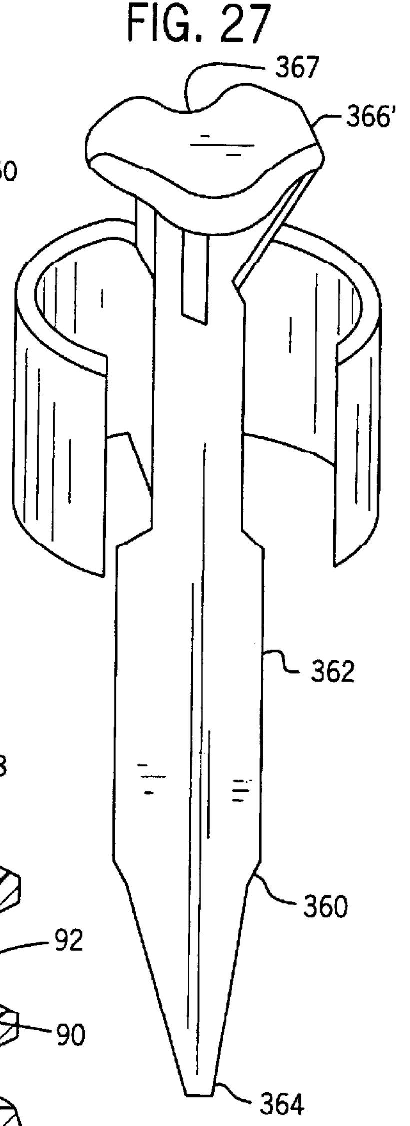
FIG. 27 is an elevational plan view of a preferred embodiment of the penetrator depicted in FIGS. 15–26.
Figure 16:
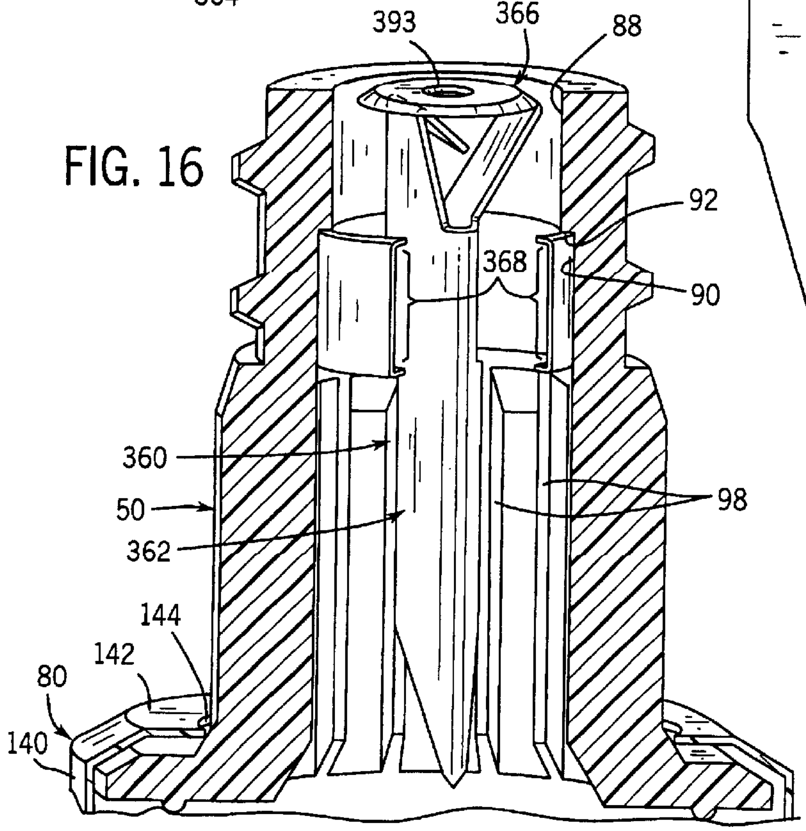
FIG. 16 is a cross-sectional perspective view of the third embodiment of the penetrator in a fully retracted position within the housing.
Figure 17:
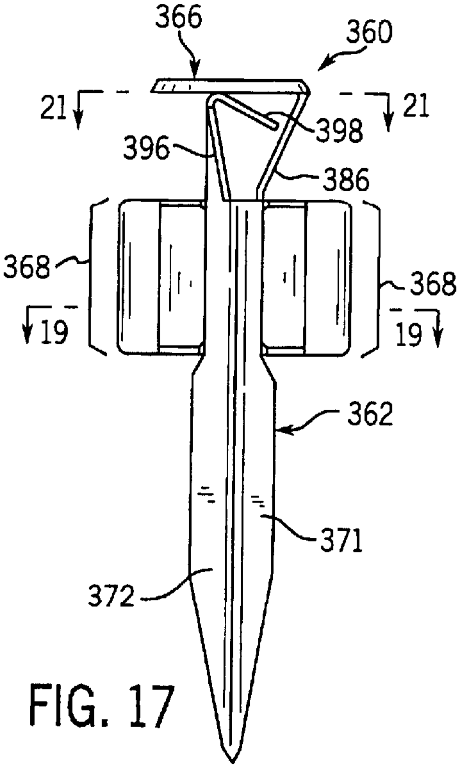
FIG. 17 is a rear elevational view of the third embodiment of the penetrator illustrated in FIGS. 15 and 16.
Figure 18:
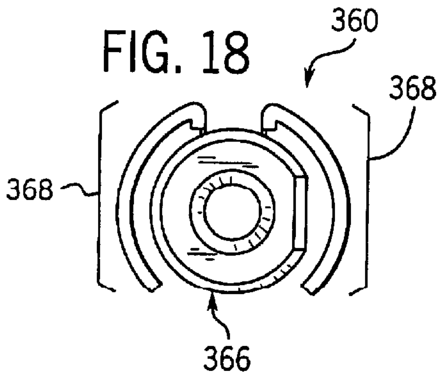
FIG. 18 is a top plan view of the third embodiment of the penetrator.

Another form of penetrator is illustrated in FIGS. 15–22 and FIG. 27 and is designated therein generally by the reference number 360. FIG. 27 depicts the preferred embodiment of this form of penetrator 360. FIGS. 15–22 reflect an alternative embodiment of penetrator 360. The embodiments of the penetrator 360 depicted in FIGS. 15–22 and FIG. 27 (hereinafter collectively referred to as "the third embodiment") are designed to be employed in the cap assembly 46 (FIG. 2) in place of the first embodiment of the penetrator 60 described above. FIG. 16 shows the third embodiment of the penetrator 360 disposed within the housing 50 of the cap assembly 46.

The third embodiment of the penetrator 360 is stamped from a piece of sheet metal, preferably stainless steel, and formed to define a shank 362 having a groove 363 extending along the length of the shank (FIG. 15), and having a pointed distal end 364. A bearing plate 366 extends from the shank 362 at an end opposite the distal end 364. Preferably, a pair of guide walls 368 extend from the shank 362 intermediate the distal end 364 and the bearing plate 366.

The shank 362 is defined by two legs 371 and 372 oriented in a generally V-shaped configuration to define an included angle of about 60° in the preferred embodiment. In the preferred embodiment, the shank pointed distal end 364 is defined by a substantially 20° included angle on each leg as indicated by the angle S in FIG. 22. The configuration of shank 362 and legs 371, 372 preferably is contingent upon the characteristics, e.g., durometer hardness value, of the stopper with which the cap assembly of the present invention is used. That is, by altering the configuration of shank 362 and legs 371, 372, it is possible to provide for a sealing of the stopper about penetrator 360 upon expiration of a predetermined period of time. Alternatively, by altering the configuration of shank 362 and legs 371, 372, it is possible to prevent the sealing of the stopper about penetrator 360 during a predetermined period of time.

Figure 19:
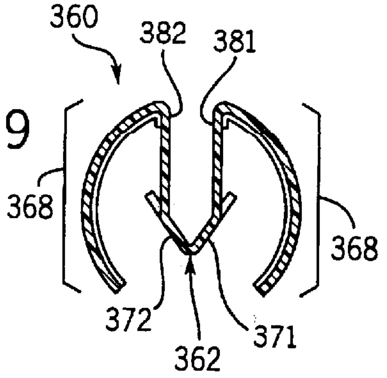
FIG. 19 is a cross-sectional view taken generally along the plane 19—19 in FIG. 17.

As best illustrated in FIG. 19, the shank 362 includes a first extension member 381 extending from the shank first leg 371 and includes a second extension member 382 extending from the shank second leg 372. The extension members 381 and 382 preferably are substantially flat, substantially parallel, and extend generally laterally for each supporting one of the guide walls 368. Each guide wall 368 is curved and substantially defines an arc of a circle.

Figure 20:
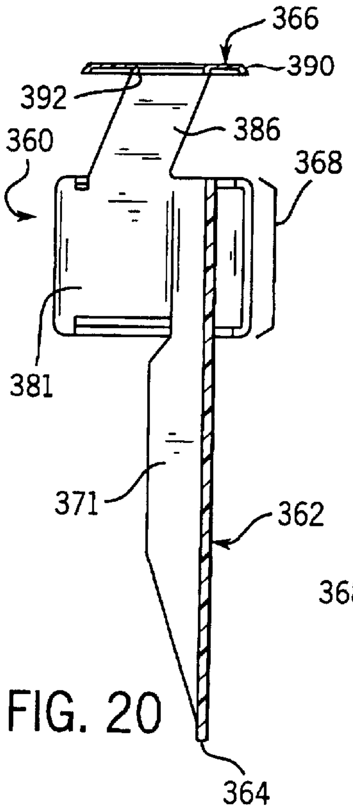
FIG. 20 is a cross-sectional view taken generally along the plane 20—20 in FIG. 18.
Figure 21:
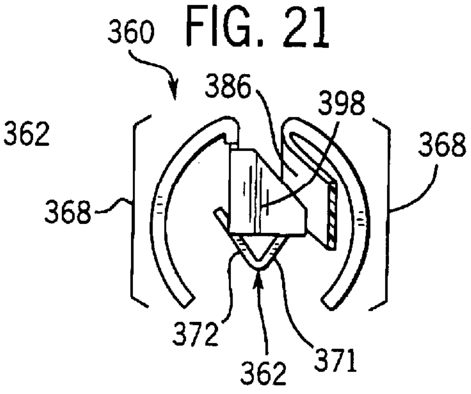
FIG. 21 is a cross-sectional view taken generally along the plane 21—21 in FIG. 17.

As can be seen in FIGS. 15, 20, and 21, a support post 386, which has a generally rectangular cross section (FIG. 21) extends upwardly, and at an oblique angle, from the extension member 381. In the preferred embodiment, support post 386 is unitary with a portion of the peripheral edge of the bearing plate 366.

In the preferred embodiment depicted in FIG. 27, bearing plate 366' does not include an aperture and is contoured to define a trough 367 along its upper surface. When bearing plate 366 is engaged by an access device such as a luer lock syringe, fluid will be able to flow around bearing plate 366', through trough 367, and into the luer lock syringe. This embodiment offers advantages in that it creates an indirect flow path for fluid being withdrawn from a container with which the cap assembly of the present invention is used. In this way, the preferred embodiment substantially prevents "spraying" of fluid from the container. This is preferable due to both safety and cost considerations.

In the alternative embodiment depicted in FIGS. 15 and 20, the bearing plate 366 has a generally annular configuration. The bearing plate 366 has an outer peripheral margin 390 bent toward the shank distal end 364. The bearing plate 366 also has an inner peripheral margin 392 bent toward the shank distal end 364. In this alternative embodiment, fluid from the container can flow both through and around bearing plate 366.

Another support post 396 extends upwardly from the second extension member 382. The post 396 has an upper end portion 398 bent over at an angle below the bearing plate 366 to define a support for the bearing plate 366.

The shank groove 363 defines a concave surface along one side of the shank. The other side of the shank defines a convex surface. The shank convex surface is more specifically defined by the outer surfaces of the legs 371 and 372, and the shank concave surface is defined by the inner surfaces of the shank legs 371 and 372. The shank legs 371 and 372, and hence the convex and concave surfaces defined by the legs, may be characterized as being oriented along a longitudinal axis. The penetrator bearing plate 366, 366' is oriented so that it is generally perpendicular to the longitudinal axis.

The stamped metal penetrator 360 is disposed in the cap assembly housing 50 so that the arcuate guide walls 368 are received within the housing lower cylindrical bore 90 (FIG. 16). The upper edge of each guide wall 368 is adapted to engage the downwardly facing annular shoulder 92 of the housing 50. This limits the upward movement of the penetrator 360 and positions the penetrator bearing plate 366, 366' within the housing bore 88.

The shank 362 of the penetrator 360 extends downwardly in the bore 90 past the guide ribs 98. The guide ribs 98 define additional flow paths past portions of the penetrator 360 when the penetrator is moved downwardly to pierce the vial stopper as explained hereinafter.

Preferably, the guide ribs 98 project slightly beyond the cylindrical surface of the lower bore 90. This provides a frictional retention means for insuring that the penetrator 360 is initially maintained in a fully retracted position within the housing 50 during assembly of the components and prior to mounting the assembly on the container 30 over the stopper 38. Additionally, there may be a friction fit between the guide walls 368 and the bore 90.

When the penetrator 360 is inserted into the housing 50, the guide walls 368 are temporarily deflected radially inwardly as the penetrator 360 is pushed up into the housing from the bottom. The housing 50 may also temporarily expand radially outwardly until the lower edges of the penetrator guide walls 368 become located above the tops of the housing ribs 98. The upper edges of the penetrator guide walls 368 are received within the bore 90 in abutting relationship with the downwardly facing annular shoulder 92 of the housing 50.

The overcap 70 (FIG. 3) and metal ferrule 80 (FIG. 3) are assembled over the housing 50 (with the penetrator 360 contained therein) in the same manner as discussed above with respect to the first embodiment of the cap assembly 46 illustrated in FIGS. 1–3. The cap assembly 46 is then mounted on, and crimped to, the container 30 as previously described.

In use, after the overcap 70 (FIG. 1) is removed, the syringe 150 is attached to the housing 50 as previously described with reference to FIG. 13. As the syringe 150 is screwed onto the housing 50, the distal end of the syringe cannula 162 engages the bearing plate 366, 366' of the penetrator 360 and forces the penetrator 360 to pierce the rubber stopper 38. The rubber stopper 38 stretches around the penetrator legs 371 and 372. The rubber stopper does not conform to the concave surface defined by the groove 363 (FIG. 15) between the two V-shaped legs 371 and 372 of the penetrator shank 362. Accordingly, there is a flow path which is established along the groove 363 of the penetrator shank 362.

When the syringe plunger 154 is withdrawn, the liquid within the vial 30 flows along groove 363 of the penetrator and through and around the bearing plate 366, 366' as above-described. The aperture 393 is generally aligned with, and is in communication with, the bore 164 defined in the cannula 162 of the syringe 150. Thus, the liquid from the vial 30 is drawn into the syringe 150.

Because the stamped metal penetrator 360 does not have a closed, cylindrical configuration, there is a reduced tendency of penetrator 360 to core out or plug out a piece of rubber from the stopper when compared to a sharp needle on a hypodermic syringe. However, as above-discussed, the durometer hardness of the stopper and the configuration of the penetrator 360 will determine whether the stopper 360 is cored and whether the flow path created by insertion of penetrator 360 will remain open during use.

Figure 23:
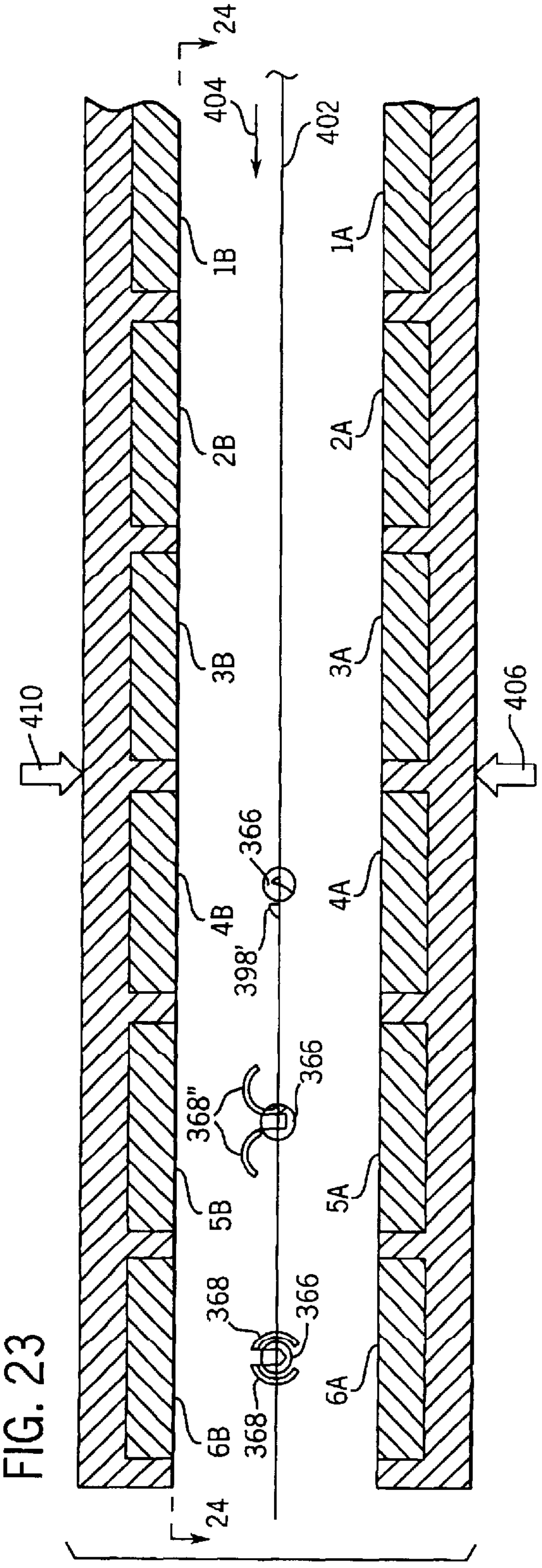
FIG. 23 is a simplified, fragmentary, partly diagrammatic, schematic illustration, partly in cross-section, generally showing the manner in which the third embodiment of the penetrator illustrated in FIGS. 14–21 is formed by the apparatus of the present invention operating according to the method of the present invention.
Figure 24:
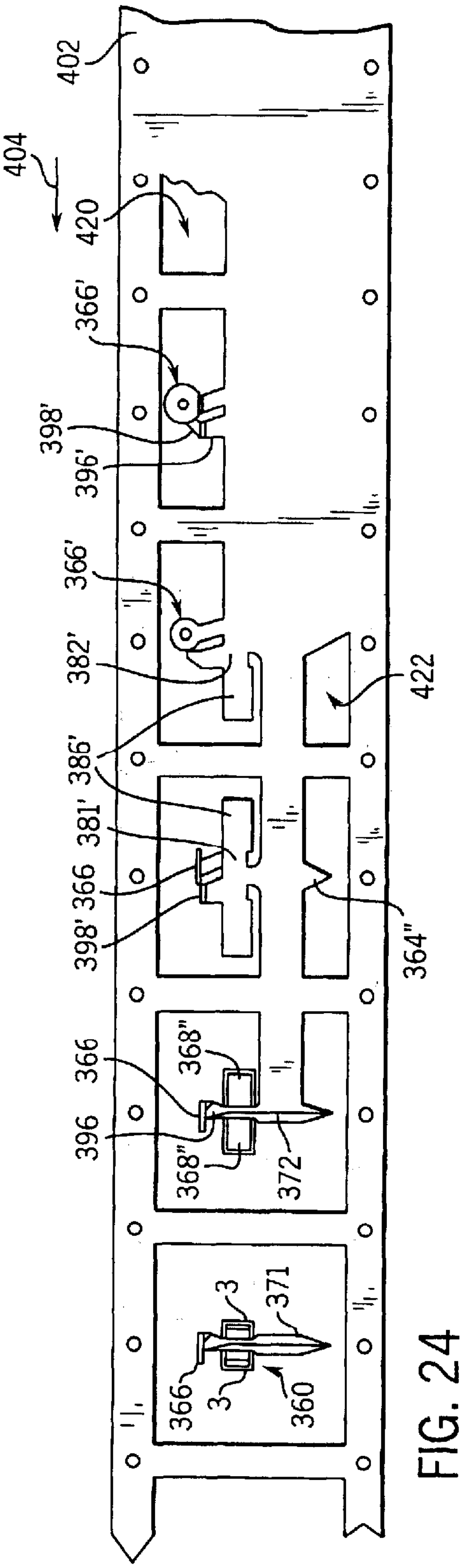
FIG. 24 is a plan view taken generally along the plane 24—24 in FIG. 23.

The design of the penetrator 360 accommodates economical manufacture by means of a progressive die containing multiple, in-line stations. According to one aspect of the present invention, a method is provided for making the penetrator utilizing a plurality of progressive die stations, each of which comprises an associated complementary punch and die as illustrated in FIGS. 23 and 24. FIGS. 23 and 24 are provided for illustrative purposes only. One of ordinary skill in the pertinent art will recognize that variations of the process depicted in FIGS. 23 and 24 are possible without departing from the spirit and scope of the present invention. For example, it will be appreciated that the number of stations can be varied.

FIG. 23 shows a planar strip of sheet metal 402 being indexed to incrementally advance progressively through six die stations in the direction of arrow 404. The strip 402 is preferably type 304 or type 316 stainless steel in the form of strip stock from a roll. The first, and most upstream, die station has a punch 1A on one side of the strip 402 and has a complementary die 1B on the other side of the strip 402. The associated punches and dies of the second through sixth stations are analogously designated with numbers 2–6, respectively.

The associated punch and die stations are progressive, and each succeeding station functions to stamp out additional portions of the strip 402 and/or deform portions of the strip to a progressively greater extent. This is effected by operating the stations (after each incremental advancement of the sheet metal strip 402) to effect relative movement between the associated punch and die of each station against the strip 402. In a preferred embodiment, the punch is moved while the die and the strip 402 are so stationary. In an alternative embodiment, the punches are moved in the direction of the arrow 406 (FIG. 23) against one side of the strip 402, and the dies are moved in the direction of the arrow 410 against the other side of the strip 402.

The mechanism for indexing the strip 402 may employ any suitable conventional or special indexing system, the details of which form no part of the present invention.

Similarly, the die stations may be provided in any suitable conventional or special punch press apparatus, the details of which form no part of the present invention. The specific configuration of the complementary die and punch in each station conforms to the particular severed and deformed portions of the strip 402 illustrated in each of the stations, respectively, in FIGS. 23 and 24.

In the preferred embodiment of the method for forming penetrator 360 of the present invention, strip 402 is introduced into two stations which consecutively punch out the perimeter of penetrator 360. At a third station, the geometry of bearing plate 366 is formed. Upper end portion 398 is then bent upwardly, as is bearing plate 366. Next, guide walls 368 and groove 363 are initially formed. Guide walls 368 are then refined in two separate steps. Guide walls 368 also are subjected to a "hemming" step in which their edges are curved to form corner radii. Next, the guide walls 368 are brought into their operative position. The groove is then brought into its final position in three steps. A final forming and a final cutting step are then provided.

In the alternative embodiment of the method of the present invention depicted in the accompanying figures, a portion of the strip 402 is severed in a closed path configuration so as to create a waste piece of the strip that defines a void 420 in the strip after removal of the waste piece. At the second station, the size of the void is increased by stamping out more of the strip material, and the bearing plate portion or preform 366' is defined, but the bearing plate portion 366' still remains generally in the plane of the strip 402. A support post portion 396' and support post end portion 398' are also stamped and defined at the second station.

Figure 22:
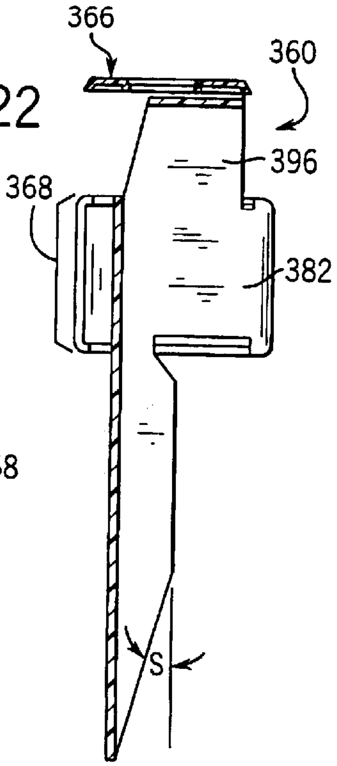
FIG. 22 is a cross-sectional view taken generally along the plane 22—22 in FIG. 18.

In the third station, a portion defining the extension member preform 382' and guide wall preform 368' are defined, but they do not yet have the final orientation or configuration of the extension member 382 and guide wall 386 shown in FIGS. 19 and 22. Additionally, in the third station, a lower void 422 is punched out.

The planar bearing plate portion 366' created in the second station is bent 90° in the fourth station so as to form the bearing plate 366. Similarly, the support post distal end portion 398' formed in station two is bent about 90° out of the plane of the strip 402 in station four.

In station four, the void 422 from station three is enlarged to define a preform 364' for the pointed distal end 364 (shown fully formed in FIG. 15).

Further, in station four, the preform of the other extension member portion 381' is formed along with the connected preform of the other guide wall portion 368'.

In station five, one side of the penetrator shank is defined by punching further material out of the strip 402. In addition, in station five the previously formed guide wall preforms 368' are further deformed into arcuate guide wall preforms 368", and the final orientations of the bearing plate 366 and the support post 396 are established. Also, the shank leg 372 is bent to its final angular orientation of about 60° out of the plane of the strip 402.

At the sixth station, the remaining connecting portion of the strip 402 is severed from the penetrator 360, and the shank leg 371 is fully defined and bent upwardly at an angle of about 60° relative to the plane of the strip 402. At the same time, the partially formed guide wall portions 368" (as previously partially formed in station five) are now fully formed into the guide walls 368 in station six.

The final, formed penetrator 360 can then be routed to an appropriate apparatus (not illustrated) for assembling the penetrator 360 with the other components to form the cap assembly 46 (FIG. 1). Any suitable conventional or special apparatus may be employed to assemble the components. The details of such an apparatus and the method of its operation form no part of the present invention.

Figure 25:
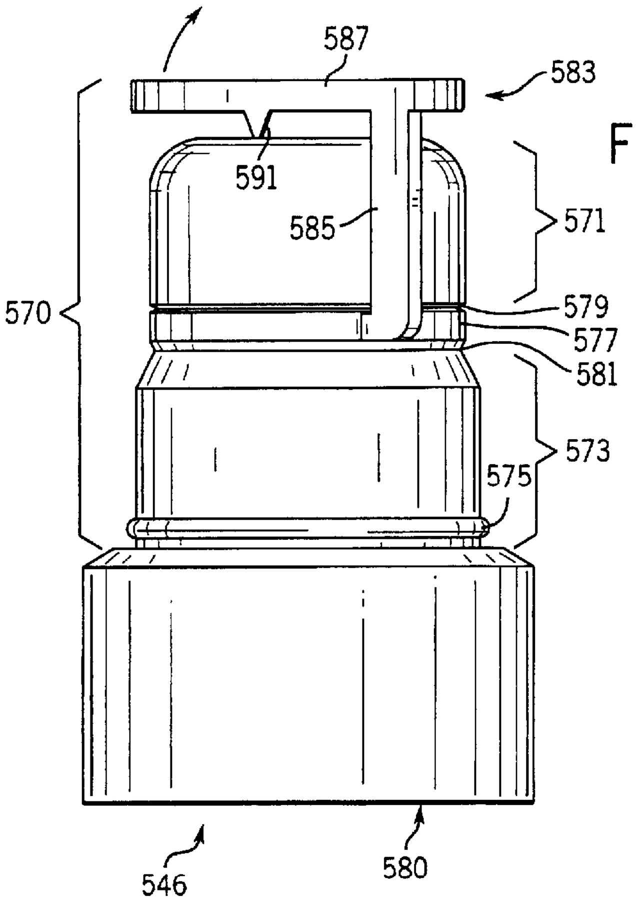
FIG. 25 is a fragmentary, perspective, view of a second embodiment of an overcap of the present invention shown as part of a cap assembly on a vial.
Figure 26:
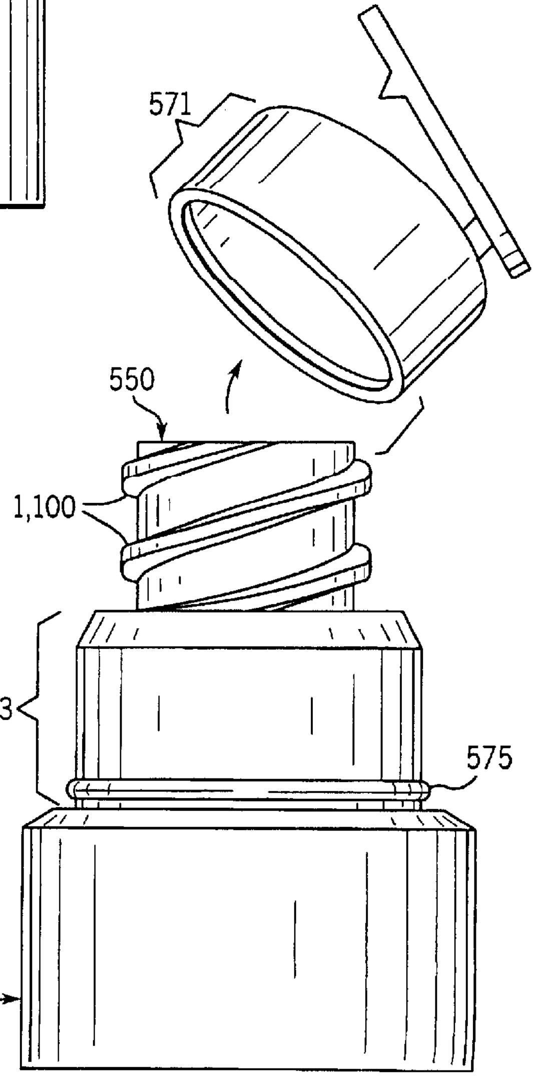
FIG. 26 is a view of the second embodiment of the overcap shown in FIG. 25 after an upper, removable portion of the overcap has been torn away to expose the upper end of an underlying housing.

Another embodiment of a cap assembly is illustrated in FIGS. 25 and 26 and is designated therein generally by the reference number 546. The cap assembly 546 has a metal ferrule 580 which, in the preferred embodiment, is substantially identical with the ferrule 80 described above with reference to the first embodiment illustrated in FIGS. 1–3.

The ferrule 580 is disposed around the base of a cap or overcap 570 (FIG. 25). The overcap 570 is disposed over a housing and penetrator contained therein. The housing and penetrator are not visible in FIG. 25, but a portion of the housing 550 is visible in FIG. 26 wherein a portion of the overcap 570 has been removed to expose the upper portion of the housing 550. The housing 550 is preferably identical with the housing 50 described above with reference to FIGS. 1–5. The penetrator is not visible within the housing 550, but the penetrator is preferably one of the three embodiments of the penetrator 60, 260, or 360 described above.

The second embodiment of the overcap 570 includes an upper part 571 and a lower part 573 below the upper part 571. The lower part 573 has a bottom end extending into the metal ferrule 580, and the bottom end of the lower part 573 preferably has a radially extending flange (not visible) which extends under the annular deck of the metal ferrule 580. Such a flange prevents removal of the overcap 570 from the assembly 546 after the assembly has been mounted to a container and after the metal ferrule 580 has been crimped around the bottom of the flange of the container or vial. Although the bottom end of the overcap 570 may have circumferentially spaced, radially extending tabs, such as the tabs 130 on the first embodiment of the overcap 70 as shown in FIG. 3, such a tab structure is not necessary in the alternate embodiment of the overcap 570. Indeed, the bottom end of the alternate embodiment of the cap 570 may be a simple, annular flange that does not include tabs such as the tabs 130 illustrated in FIG. 3 for the first embodiment of the overcap 70.

Preferably, the lower part 573 of the alternate embodiment of the overcap 570 includes a radially outwardly extending retention bead 575. This facilitates the assembly of the components. In particular, the metal ferrule 580 can be forced over the bead 575. The metal ferrule 580 temporarily expands outwardly a slight amount or the bead 579 deflects inwardly a small amount as the ferrule moves past the bead 575. Then, during further processing of the cap assembly 546, the metal ferrule 580 is retained between the bead 575 and the bottom flange (not visible) on the overcap 570.

The overcap 570 includes a circumferential tear ring 577 connecting the upper part 571 to the lower part 573. Preferably, the overcap 570 is molded as a unitary structure from plastic material, such as polyethylene or the like. The top edge of the tear ring 577 is connected to the overcap upper part 571 with a reduced thickness of material which defines an annular groove 579. Similarly, the bottom edge of the tear ring 577 is connected to the top of the overcap lower part 573 with a reduced thickness of material defining an annular groove 581. The grooves 579 and 581 function as circumferential lines of weakness defining frangible connections.

Preferably, a pull tab 583 extends from the tear ring 577. The pull tab 583 is molded as part of the unitary structure of the overcap 570. Preferably, the pull tab 583 includes a first, vertically extending post 585 which has a bottom end directly merging with the tear ring 577. The upper end of the post 585 merges with a stabilizing bar 587 which is connected to the top of the overcap upper part 571 with a small, generally V-shaped, frangible connecting member 591.

The connecting member 591 is molded as an extension between the stabilizing bar 587 and the top of the overcap upper part 571. The member 591 is unitary with both the stabilizing bar 587 and the overcap upper part 571. The lower, pointed end of the connecting member 591 is relatively small, and is therefore easily broken away from the top of the overcap upper part 571.

The stabilizing bar 587 may be grasped between the thumb and index finger and lifted upwardly to rupture the connection between the connecting member 591 and the top of the overcap upper part 571. The pull tab 583 may then be pulled radially outwardly to effect separation of the tear ring 577 from the overcap upper part 571 and lower part 573. If desired, the stabilizing bar 587 may be provided in the form of an annular pull ring.

After the tear ring 577 is torn away, the overcap upper part 571 falls away, or can be lifted away, to expose the upper portion of the housing 550. The upper portion of the housing 550 preferably includes a conventional luer lock dual thread formation 1,100 for engaging a mating luer lock thread on a syringe or other suitable fluid transfer device.

It will be readily apparent from the foregoing detailed description of the invention and from the illustrations thereof that numerous variations and modifications may be effected without departing from the true spirit and scope of the novel concepts or principles of this invention.

What is claimed is:

1. A cap assembly for a container having a stopper, said cap assembly comprising:

a hollow housing having an upper end portion adapted to receive a fluid transfer device in sealed communication and a lower end portion adapted to be mounted adjacent a top end of a stopper sealing a container, the lower end portion having a radially outwardly extending portion extending therefrom and a downwardly extending element to engage a stopper, and an internal cavity open at the upper end portion and at the lower end portion;

a penetrator received in the internal cavity, the penetrator having a pointed distal end opposite a stopper and an upper end constructed to be engaged by a fluid transfer device inserted into the internal cavity;

a removable cap constructed to cover the hollow housing, the cap having a closed end and an open end, the cap having a radially outwardly extending portion extending therefrom at the open end; and a ferrule having a first portion disposed over the radially outwardly extending lower end portion of the hollow housing and over the radially outwardly extending portion of the cap.

2. The cap assembly for a container in accordance with claim 1 wherein the penetrator further includes a groove providing communication between the container and the housing when the penetrator penetrates the stopper.

3. The cap assembly for a container in accordance with claim 2 wherein the groove is v-shaped.

4. A cap assembly for a container having a stopper, said cap assembly comprising:

a hollow housing having an upper end portion adapted to receive a fluid transfer device in sealed communication and a lower end portion adapted to be mounted adjacent a top end of a stopper sealing a container, the lower end portion having a radially outwardly extending portion extending therefrom, and an internal cavity open at the upper end portion and at the lower end portion;

a penetrator received in the internal cavity, the penetrator having a pointed distal end opposite a stopper and an upper end constructed to be engaged by a fluid transfer device inserted into the internal cavity; and a cap comprising an upper part having a closed end enclosing the upper and portion of the housing and the upper end of the penetrator, a lower part having an open end, the open end having a radially outwardly extending portion extending therefrom, and a circumferential line of weakness connecting the upper and lower parts of the cap for removing the upper part of the cap to expose the upper portion of the housing.

5. The cap assembly for a container in accordance with claim 4 further comprising:

a ferrule having a first portion disposed over the radially outwardly extending lower end portion of the housing and over the radially outwardly extending portion of the cap.

6. The cap assembly for a container in accordance with claim 4, wherein the lower end portion of the housing includes a downwardly extending element to engage a stopper.

7. The cap assembly for a container in accordance with claim 4, wherein the penetrator further includes an external groove providing communication between the container and the housing when the penetrator pierces the stopper.

8. A cap assembly for a container, said cap assembly comprising:

a hollow housing having an upper end portion adapted to receive a fluid transfer device in scaled communication and a lower end portion adapted to be mounted adjacent a top end of a stopper sealing the container, the lower and portion having a radially outwardly extending portion extending therefrom, and an internal cavity open at the upper end portion and at the lower end portion;

a penetrator received in the internal cavity, the penetrator having a pointed distal end opposite the stopper and an upper end constructed to be engaged by the fluid transfer device inserted into the internal cavity;

a cap comprising an upper part having a closed end enclosing the upper end portion of the housing and the upper end of the penetrator, a lower part having an open end, and a circumferential line of weakness connecting the upper and lower parts of the cap for removing the upper part of the cap to expose the upper portion of the housing.

* * * * *

UNITED STATES PATENT AND TRADEMARK OFFICE

CERTIFICATE OF CORRECTION

PATENT NO. : 6,635,043 B2
DATED : October 21, 2003
INVENTOR(S) : Richard F. Daubert et al.

It is certified that error appears in the above-identified patent and that said Letters Patent is hereby corrected as shown below:

Title page,
Item [57], ABSTRACT,
Line 9, after “constructed” insert therefore -- to cover --

Column 18,
Line 15, after “upper” delete “and” and insert therefore -- end --

Column 19,
Line 21, after “in” delete “scaled” and insert therefore -- sealed --

Column 20,
Line 4, before “portion” delete “and” and insert therefore -- end --

Signed and Sealed this

Fifth Day of April, 2005

JON W. DUDAS
*Director of the United States Patent and Trademark Office*